United States Patent
Tanaka

(10) Patent No.: US 10,178,360 B2
(45) Date of Patent: Jan. 8, 2019

(54) IMAGING SENSOR COUPLED WITH LAYERED FILTERS

(71) Applicants: SONY CORPORATION, Tokyo (JP); SONY PICTURES ENTERTAINMENT INC., Culver City, CA (US)

(72) Inventor: Kazunori Tanaka, Irvine, CA (US)

(73) Assignees: SONY CORPORATION, Tokyo (JP); SONY PICTURES ENTERTAINMENT INC., Culver City, CA (US)

(*) Notice: Subject to any disclaimer, the term of this patent is extended or adjusted under 35 U.S.C. 154(b) by 0 days.

(21) Appl. No.: 14/817,087

(22) Filed: Aug. 3, 2015

(65) Prior Publication Data

US 2017/0041574 A1    Feb. 9, 2017

(51) Int. Cl.
| | |
|---|---|
| H04N 1/48 | (2006.01) |
| H04N 9/04 | (2006.01) |
| H04N 9/07 | (2006.01) |
| G01N 21/31 | (2006.01) |
| G01N 21/64 | (2006.01) |

(52) U.S. Cl.
CPC .............. *H04N 9/045* (2013.01); *H04N 1/482* (2013.01); *H04N 9/07* (2013.01); *G01N 2021/3174* (2013.01); *G01N 2021/6471* (2013.01); *H04N 2209/043* (2013.01)

(58) Field of Classification Search
None
See application file for complete search history.

(56) References Cited

U.S. PATENT DOCUMENTS

| | | | | |
|---|---|---|---|---|
| 6,035,144 | A | * | 3/2000 | Gfeller ...................... G03B 9/08 348/E5.024 |
| 7,535,504 | B2 | | 5/2009 | Frame et al. |
| 2002/0030755 | A1 | * | 3/2002 | Uchino ................ H04N 5/2254 348/342 |
| 2003/0098918 | A1 | * | 5/2003 | Miller .................... H04N 9/045 348/273 |
| 2008/0030803 | A1 | | 2/2008 | Min et al. |

(Continued)

FOREIGN PATENT DOCUMENTS

| | | |
|---|---|---|
| CN | 101213830 A | 7/2007 |
| CN | 101119445 A | 2/2008 |

(Continued)

OTHER PUBLICATIONS

Office Action issued in copending Chinese Application No. 201610626257.7 dated Sep. 4, 2017 in 10 pages.

*Primary Examiner* — Justin P. Misleh

(74) *Attorney, Agent, or Firm* — Procopio, Cory, Hargreaves & Savitch LLP

(57) ABSTRACT

A digital imaging device includes: a monochromatic sensor including a plurality of photosensitive elements distributed in an array, the plurality of photosensitive elements configured to convert light falling on the monochromatic sensor into electronic signals; and a plurality of filters, each filter configured to be moved into a position in front of the monochromatic sensor, wherein each filter, when moved into the position in front of the monochromatic sensor, covers substantial portion of the monochromatic sensor. Key words include imaging sensor and layered filter.

13 Claims, 4 Drawing Sheets

(56) References Cited

U.S. PATENT DOCUMENTS

| | | | | |
|---|---|---|---|---|
| 2008/0123097 A1* | 5/2008 | Muhammed | ............ | G01J 3/02 |
| | | | | 356/419 |
| 2008/0246856 A1* | 10/2008 | Shibuya | ............... | H04N 9/045 |
| | | | | 348/223.1 |
| 2009/0244355 A1* | 10/2009 | Horie | ..................... | G02B 5/22 |
| | | | | 348/340 |
| 2011/0150331 A1 | 6/2011 | Young | | |
| 2015/0070563 A1* | 3/2015 | Sperber | ................ | G02B 7/005 |
| | | | | 348/342 |
| 2015/0334357 A1* | 11/2015 | Wang | ................... | H04N 9/045 |
| | | | | 348/278 |
| 2016/0171653 A1* | 6/2016 | Mendlovic | ............... | G01J 3/26 |
| | | | | 348/280 |
| 2016/0205373 A1* | 7/2016 | Ando | ................... | H04N 9/045 |
| | | | | 348/270 |

FOREIGN PATENT DOCUMENTS

| CN | 101878653 A | 11/2010 |
|---|---|---|
| CN | 102365860 A | 2/2012 |
| CN | 102396235 A | 3/2012 |

\* cited by examiner

IMAGING SENSOR COUPLED WITH LAYERED FILTERS

BACKGROUND

Field of the Invention

The present disclosure relates to imaging sensors, and more specifically, to an imaging sensor coupled with layered filters.

Background

FIG. 1A shows a typical digital imaging device 100 including a lens 120 (or lens system) and an image sensor 130. In FIG. 1A, an object 110 reflects light 112 that is focused by the lens 120 onto an image sensor 130 as an image object 114. The image sensor 130 includes photosensitive elements or sensels 132 which are distributed over the surface of the image sensor 130 in a two-dimensional array. The sensels 132 generally convert the light focused onto the surface of the image sensor 130 by the lens 120 (i.e. the image object 114) into electronic signals.

A digital camera includes a sensor to capture the color signal of objects using a color filter array (CFA), which has one color filter element for each sensel. Thus, the color filter element manages one color sample at a time. The CFA is used to capture all three color channels at the same time and reduce the complexity and cost of the digital cameras. Thus, in a conventional color imaging device, each of the sensels 132 receives light within one of three overlapping frequency bands. The relative intensity of the light received by an individual sensel 132 included in a group of sensels 140 (in which each of the different frequency bands are represented) enables the image sensor 130 to provide color information.

FIG. 1B illustrates a Bayer pattern which is widely-used CFA pattern. The sampling of green (G) color component 142 is twice as many as compared to each of red (R) 144 and blue (B) 146 color components. As shown in FIG. 1B, at each pixel (configured with a sensel), only one color component is present. The missing two colors have to be interpolated from the existing pixels. The process of reconstructing a full resolution color image from Bayer sample is known as demosaicing. An inherent limitation in the interpolation process leads to visual artifacts that appear around edges and color mis-registration artifacts that degrade the color resolution. Thus, the reconstruction of the color image from the data attained by the monochromatic sensor filtered by the CFA (e.g., in a demosaicing process) results in a loss of spatial resolution.

SUMMARY

The present disclosure combines various photographic workflows as well as physical components of photography in a relatively low-cost way that allows for the best image quality. The combination is configured to provide better spatial and tonal resolution, but at the expense of capturing speed.

In one implementation, a digital imaging device is disclosed. The digital imaging device includes: a monochromatic sensor including a plurality of photosensitive elements distributed in an array, the plurality of photosensitive elements configured to convert light falling on the monochromatic sensor into electronic signals; and a plurality of filters, each filter configured to be moved into a position in front of the monochromatic sensor, wherein each filter, when moved into the position in front of the monochromatic sensor, covers substantial portion of the monochromatic sensor.

In another implementation, an apparatus is disclosed. The apparatus includes: multiple means for photo-sensing distributed in an array and configured to convert light incident on the multiple means for photo-sensing into electronic signals; and multiple means for filtering, each means for filtering configured to be moved into a position in front of the multiple means for photo-sensing, wherein each means for filtering, when moved into the position in front of the multiple means for photo-sensing, covers substantial portion of the multiple means for photo-sensing.

In another implementation, a method is disclosed. The method includes: selecting and moving a first filter of a plurality of filters into a position in front of a monochromatic sensor; capturing and storing a first image corresponding to the first filter by the monochromatic sensor into a storage unit; selecting and moving a second filter of the plurality of filters into the position in front of the monochromatic sensor; and capturing and storing a second image corresponding to the second filter by the monochromatic sensor into the storage unit.

Other features and advantages of the present disclosure should be apparent from the present description which illustrates, by way of example, aspects of the disclosure.

BRIEF DESCRIPTION OF THE DRAWINGS

The details of the present disclosure, both as to its structure and operation, may be gleaned in part by study of the appended further drawings, in which like reference numerals refer to like parts, and in which:

FIG. 1 shows a typical digital imaging device including a lens (or lens system) and an image sensor;

DETAILED DESCRIPTION

Figures 1A, 1B:
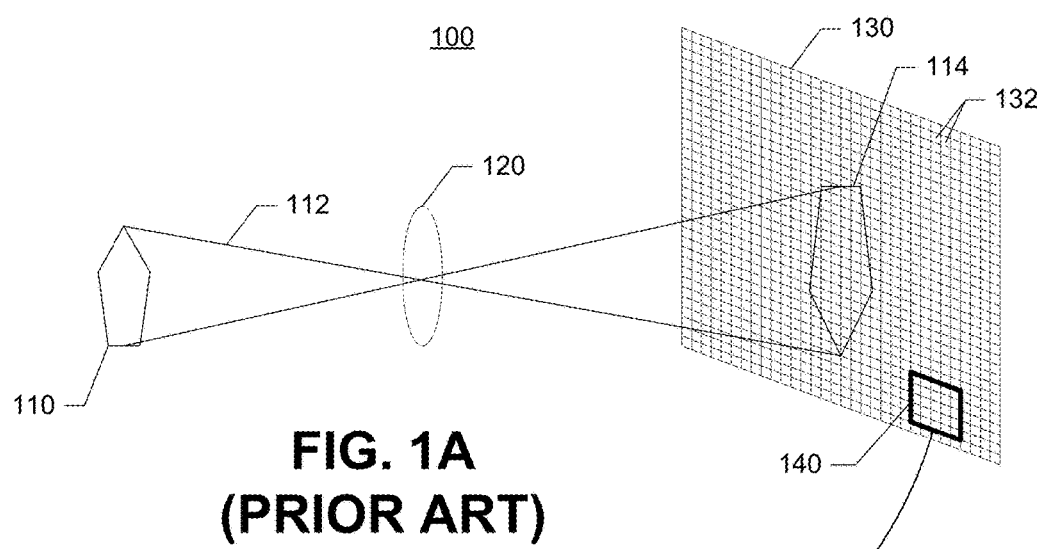
FIG. 1B illustrates a Bayer pattern which is widely-used CFA pattern.

As stated above, the reconstruction of the color image from the data attained by the monochromatic sensor filtered by the CFA (e.g., in a demosaicing process) results in a loss of spatial resolution. Furthermore, because each sensel is limited to acquiring only those photons that pass through the filter assigned to it in the CFA, the overall light sensitivity is lowered (e.g., by about one-third). However, for a general use, especially for photography of moving subjects, low sensitivity is inconvenient and undesirable. Thus, the colors in the CFA are chosen in a way that is less color-sensitive so that more light reaches the sensor. This results in an increased light sensitivity at the cost of decreased color accuracy. Therefore, both the loss of resolution and color accuracy are tradeoffs for increased sensitivity (or shortened capture time) and convenience. Accordingly, a camera that is optimized for image quality (at the cost of sensitivity) with better tonal and spatial resolution (as well as color fidelity) would be convenient and desirable for uses that do not require fast acquisition.

Another issue with the conventional digital imaging device is the inclusion of an ultra-violet (UV)/infra-red (IR) block filter in front of the image sensor. However, to take images in the IR or a broader spectrum than our visual range (i.e., full-spectrum), the digital imaging device needs a sensor without the UV/IR block filter. Since the UV/IR block filter is needed in the digital camera to take ordinary color images, a second modified camera is needed to take IR or full-spectrum images, in addition to the ordinary color images. A monochromatic or black-and-white camera, which has the full resolution of a sensor without a CFA, has the same issue of needing a second camera to take ordinary color images. Accordingly, a camera that can take IR, full-spectrum, monochromatic, and ordinary color images, while benefitting from the full resolution of a sensor without a CFA, would be desirable.

Yet another issue with the conventional digital imaging device involves filters, which are used for many reasons in the digital imaging device. For example, polarizing filters, neutral density filters, color and IR filters of various types can be used, separately or in combination, to change the image that reaches the sensor (i.e, the image object). The filters are typically configured to be in front of the lens. The problem with this configuration of filters is that the imaging device gets more bulky as more filters are stacked in front of the lens. This configuration also causes greater chance of "image vignetting," which is a reduction in the brightness or saturation at the periphery compared to the center of an image due to the filter housings. Another issue with external filters is the contamination from the surroundings, which decreases the final image quality. Further, a set of various filters can be expensive, and this multiplies because a set is needed for each lens that has a different filter size. Accordingly, a camera that is optimized for image quality (even if it is a little slower in operation compared to general-use cameras) would be useful for situations that do not require speed of operation, such as capturing landscape, art, and product photography, in addition to other creative uses. Further, a camera that houses many useful filters and changes them automatically and independently (so that they can be used in combination) would be convenient for a user, as it saves space, cost, and operation time, while improving the image quality. The convenience and utility for such a camera can be increased if it can also be used as an IR, full-spectrum, and monochromatic camera.

Certain implementations as disclosed herein combine various photographic workflows as well as physical components of photography in a relatively low-cost way that allows for the best image quality. The combination is configured to provide better spatial and tonal resolution, but at the expense of capturing speed. Further, some embodiments include versatile spectral selectivity for both creativity and color accuracy, while substantially reducing the need to carry so many camera bodies, filters, and lenses, as well as the need to manage them. After reading this description it will become apparent how to implement the disclosure in various implementations and applications. However, although various implementations of the present disclosure will be described herein, it is understood that these implementations are presented by way of example only, and not limitation. As such, this detailed description of various implementations should not be construed to limit the scope or breadth of the present disclosure.

Figure 2:
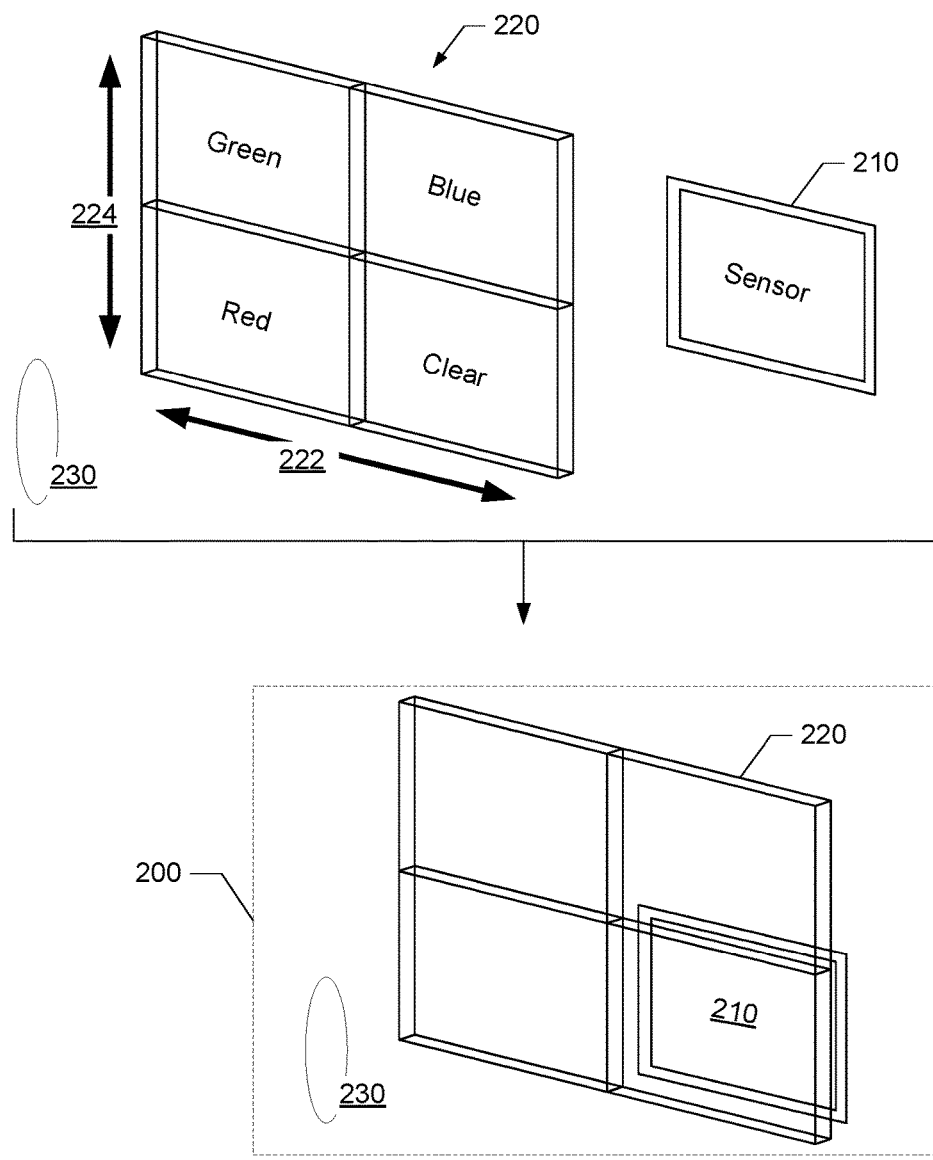
FIG. 2 is a block diagram of a digital imaging device in accordance with one implementation of the present disclosure.

FIG. 2 is a block diagram of a digital imaging device 200 in accordance with one implementation of the present disclosure. The digital imaging device 200 includes a plurality of filters 220 configured to be placed in between lens(es) 230 and a sensor 210. In the illustrated implementation of FIG. 2, the plurality of filters 220 is shifted (either horizontally 222 or vertically 224) such that a filter (i.e., one of green, red, blue, or clear filter) of the plurality of filters 220 is placed into a position directly in front of the sensor 210. In one implementation, the sensor 210 is a monochromatic sensor similar to the image sensor 130 in FIG. 1A, without the attachment of the color filter array (CFA).

In the illustrated implementation of FIG. 2, the use of the monochromatic sensor 210 substantially reduces the problem with the reduction of resolution caused by the use of the CFA. The use of the monochromatic sensor 210 also allows the plurality of filters 220 to be used with any lens, which cuts down on the number of filters that needs to be carried separately for each lens. Further, since the filters 220 are internal to the digital imaging device 200, the implementation of FIG. 2 keeps filters 220 clean by avoiding the need to replace them and exposing them to the air.

In another implementation, the monochromatic sensor 210 can be configured as any type of multiple means for photo-sensing distributed in an array and configured to convert light incident on the multiple means for photo-sensing into electronic signals. For example, the multiple means for photo-sensing can be configured with complementary metal oxide semiconductor (CMOS) sensors, charge-coupled device (CCD) sensors, or linear sensors. In yet another implementation, the plurality of filters 220 can be configured as any type of multiple means for filtering, with each means for filtering configured to be moved into a position in front of the monochromatic sensor 210. Thus, when each means for filtering is moved into the position in front of the monochromatic sensor, each means for filtering covers substantial portion of the monochromatic sensor. In one implementation, each means for filtering is configured with an optical filter, photographic filter, absorptive filter, or dichroic filter. In a further implementation, the multiple means for filtering are arranged in multiple layers, wherein each layer has at least one means for filtering.

Figure 3:
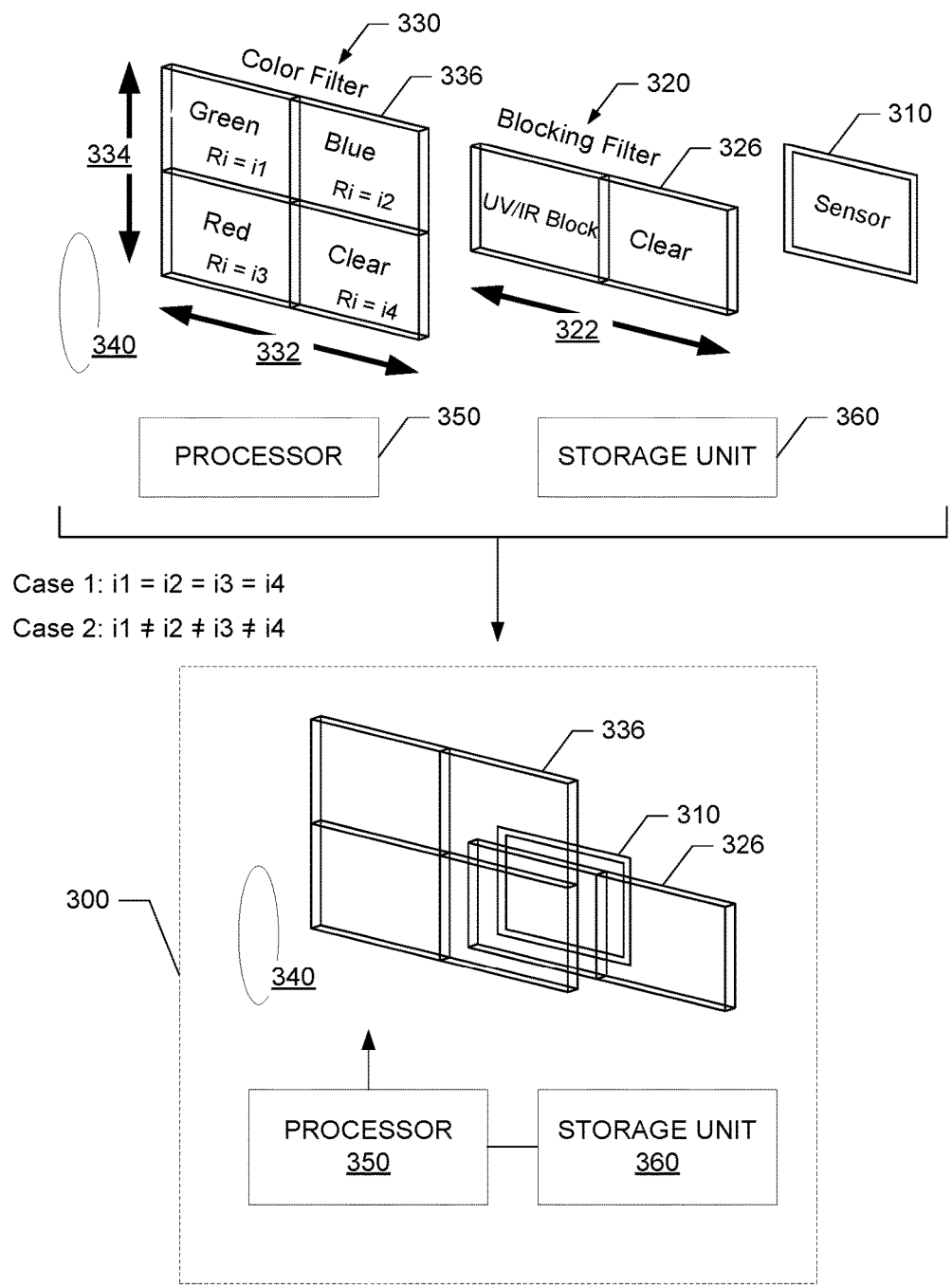
FIG. 3 is a functional block diagram of a digital imaging device in accordance with another implementation of the present disclosure in which filters are organized into layers.

FIG. 3 is a functional block diagram of a digital imaging device 300 in accordance with another implementation of the present disclosure in which filters are organized into layers. The digital imaging device 300 includes a sensor 310, a plurality of filters 326, 336, lenses 340, a processor 350, and a storage unit 360. In the illustrated implementation of FIG. 3, the plurality of filters 326, 336 is organized into two layers, a color filter layer 330 and a blocking filter layer 320.

The blocking filter layer 320 includes a plurality of blocking filters 326 such as an ultraviolet (UV) blocking filter, an infrared (IR) blocking filter, a UV/IR blocking filter, a UV/IR pass filter, a clear filter (which is equivalent to no blocking filter), and other similarly-implemented blocking filters (e.g., a mid-band blocking filter). In one implementation in which the blocking filter layer 320 is configured with a UV/IR blocking filter placed or switched in front of the sensor 310, the digital imaging device 300 is configured as a standard digital camera. In another implementation in which the blocking filter layer 320 is configured with a clear filter placed or switched in front of the sensor 310, the digital imaging device 300 lets through more wavelengths of light, and is configured as a full-spectrum camera. In yet another implementation, with an IR pass filter switched in front of the sensor 310, the digital imaging device 300 is configured as an IR camera. The color filter layer 330 includes a plurality of color filters 336 such as a green filter, a red filter, a blue filter, a clear filter (which is equivalent to no color filter), and other similarly-implemented color filters (e.g., a magenta filter).

In other implementations, the filters can be organized into more than two layers with each layer including a different type of filters. Each layer can include, but is not limited to, a blocking filter layer, a color filter layer, a polarizing filter layer, or a neutral density filter layer. For another example, the neutral density filter layer can be configured to switch between neutral density filters of various strengths to attenuate the light. These filters can be used to not only slow down the optical speed for artistic reasons, but also take shots of the same scene using different neutral density filters and combine them to create a high-dynamic range image automatically. Since each layer works independently, the filters in different layers can be used together. For example, a UV/IR block filter in the blocking filter layer 320 can be used in combination with a blue filter in the color filter layer 330. In another example, a circular polarizer filter can be used along with a clear blocking filter (to get full-spectrum), but by merging images taken with combinations of color filters (red, green, blue, magenta, yellow, cyan to get a wide color gamut) and various neutral density filters (to get high-dynamic range data), a high-dynamic range wide-color gamut full-spectrum image that is polarized can be created.

Further, in one implementation, all filters within one layer are configured to have the same index of refraction so that the optical path length, which is wavelength dependent, is maintained to keep substantially the same focusing distance. In another implementation, filters in one layer are configured to have different indices of refraction, but with the location of the sensor in relation to the rest of the system adjusted so that the optical path length is still maintained.

In the illustrated implementation of FIG. 3, the plurality of filters 326 in a first layer (i.e., the blocking filter layer) 320 can be shifted horizontally 322 such that a filter (i.e., one of UV/IR blocking filter or clear filter) of the plurality of filters 326 is shifted or placed into a position in front of the sensor 310. Further, the plurality of filters 336 in a second layer (i.e., the color filter layer) 330 can be shifted horizontally 332 or vertically 334 such that a filter (i.e., one of green, red, blue, or clear filter) of the plurality of filters 336 is shifted or placed into a position in front of the selected filter of the first layer 320, which is shifted or placed in front of the sensor 310. The selection and movement of the filters 326, 336 are performed by the processor 350. Since the selection and movement of the filters 326, 336 are all performed within the digital imaging device 300, the amount of time needed for the filter management can be substantially reduced.

Although adding layers of filters can expand the capabilities of a digital imaging device, adding filters within the single optical path can result in image degradation. Therefore, if a layer is not needed, it can be removed so that there is nothing for that layer. However, the sensor location needs to be adjusted to make up for the removed layer because the optical path would be changed otherwise. Conversely, given that a camera lens system already has lenses designed for a certain thickness of filters in front of the sensor, the digital imaging device of the present disclosure is designed so that the sum of the thickness of all the filter layers will equal a fixed number for which the lenses were designed. That is, adding additional filter layers will require the thickness of each filter layer to be reduced. For example, if a sensor filter stack for a certain brand is 2 mm thick, having four layers may mean making each layer only be 0.5 mm thick, while having two layers may mean making each layer be 1 mm.

Figure 4A:
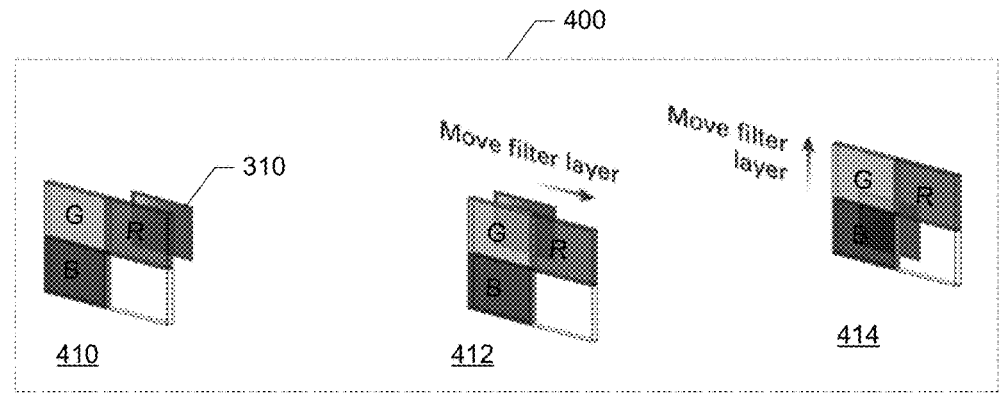
FIG. 4A shows a process in which a color filter layer is shifted horizontally or vertically to place a color filter into a position in front of the sensor.
Figure 4B:
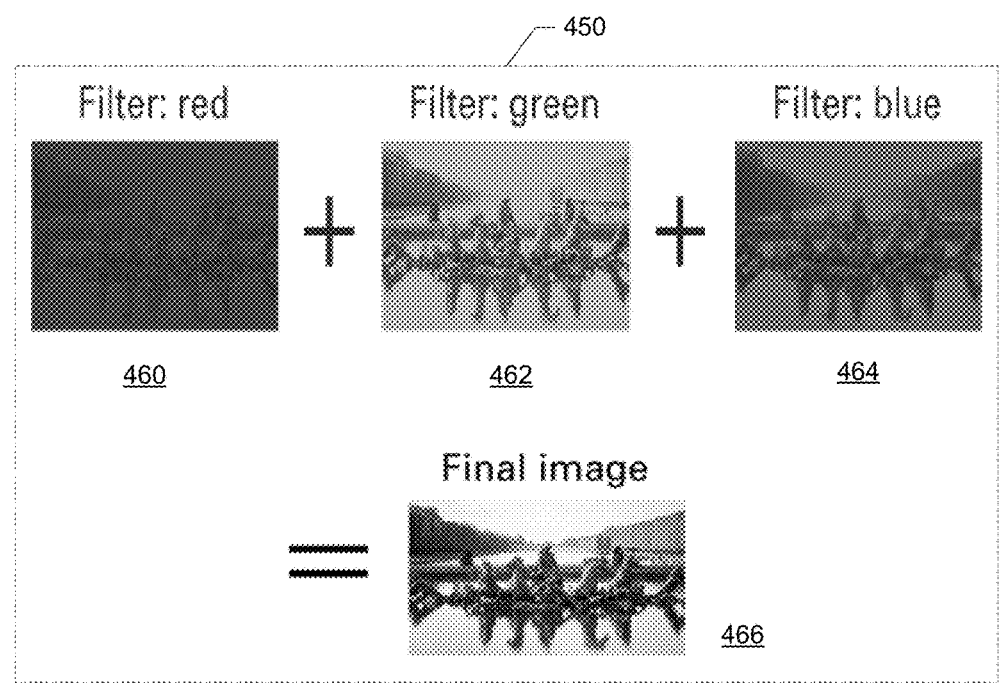
FIG. 4B shows a process by which images of component colors are captured by the sensor, and subsequently merged to create a color image.

FIGS. 4A and 4B show processes 400, 450 in which the color information is obtained using a monochromatic sensor coupled to at least one color filter layer in accordance with one implementation of the present disclosure.

The illustrated implementation of FIG. 4A shows the process 400 in which a color filter layer is shifted horizontally or vertically to place a color filter into a position in front of the sensor 310. For example, step 410 illustrates a red filter placed in a position in front of the sensor 310. The color filter layer is shifted horizontally, at step 412, to place a green filter in a position in front of the sensor 310. The color filter layer is then shifted vertically, at step 414, to place a blue filter in a position in front of the sensor 310.

The illustrated implementation of FIG. 4B shows the process 450, in which, during each of steps 460, 462, 464, an image is captured by the sensor 310 with a selected color. At each step 460, 462, or 464, the captured image is also stored in a storage unit. For example, at step 460, a first image is captured by the sensor 310 with a red color which is enabled by the selection of the red color filter performed at step 410. A second image is captured, at step 462, by the sensor 310 with a green color which is enabled by the selection of the green color filter performed at step 412. A third image is captured, at step 464, by the sensor 310 with a blue color which is enabled by the selection of the blue color filter performed at step 414. Then, at step 466, the three captured and stored images (e.g., images are stored in the storage unit 360) are composited to produce an output image (i.e., a final color image). In one implementation, the images are composited by the processor 350 in-camera. In another implementation, the images are composited during post processing.

Because multiple images are being taken in the illustrated implementations of FIGS. 4A and 4B, the integration time of data acquisition of the digital imaging device is longer, but the final result includes more tonal resolution. Further, the exposure time for each color pass can be independently controlled to substantially improve or optimize the use of the saturation capacity of the sensor. For example, if a scene does not include much blue color, the exposure time for the blue color can be extended longer to improve the signal-to-noise ratio for the blue color channel.

In a further implementation, the color filter layer is configured to include red, green, and blue filters, but is also enabled to allow for greater color accuracy by having an option to expand the gamut of the input color space to include other color filters such as cyan, magenta, and yellow filters. The red, blue, and green filters could also be chosen to be more pure, allowing for the capture of wider-gamut images.

The foregoing devices, methods, and apparatus are susceptible to many variations. Additionally, for clear and brief description, many descriptions of the devices, methods, and apparatus have been simplified. Many descriptions use terminology and structures of specific standards. However, the disclosed devices, methods, and apparatus are more broadly applicable.

Those of skill in the art will appreciate that the various illustrative logical blocks, modules, units, and algorithm steps described in connection with the embodiments disclosed herein can often be implemented as electronic hardware, computer software, or combinations of both. To clearly illustrate this interchangeability of hardware and software, various illustrative components, blocks, modules, and steps have been described above generally in terms of their functionality. Whether such functionality is implemented as hardware or software depends upon the particular constraints imposed on the overall system. Skilled persons can implement the described functionality in varying ways for each particular system, but such implementation decisions should not be interpreted as causing a departure from the scope of the disclosure. In addition, the grouping of functions within a unit, module, block, or step is for ease of description. Specific functions or steps can be moved from one unit, module, or block without departing from the disclosure.

The steps of a method or algorithm and the processes of a block or module described in connection with the embodiments disclosed herein can be embodied directly in hardware, in a software module executed by a processor, or in a combination of the two. A software module can reside in RAM memory, flash memory, ROM memory, EPROM memory, EEPROM memory, registers, hard disk, a removable disk, a CD-ROM, or any other form of storage medium. An exemplary storage medium can be coupled to the processor such that the processor can read information from, and write information to, the storage medium. In the alternative, the storage medium can be integral to the processor. The processor and the storage medium can reside in an ASIC. Additionally, device, blocks, or modules that are described as coupled may be coupled via intermediary device, blocks, or modules.

The above description of the disclosed implementations is provided to enable any person skilled in the art to make or use the disclosure. Various modifications to these implementations will be readily apparent to those skilled in the art, and the generic principles described herein can be applied to other embodiments without departing from the spirit or scope of the disclosure. Accordingly, the techniques are not limited to the specific examples described above. Thus, it is to be understood that the description and drawings presented herein represent a presently preferred embodiment of the disclosure and are therefore representative of the subject matter that is broadly contemplated by the present disclosure. It is further understood that the scope of the present disclosure fully encompasses other embodiments that may become obvious to those skilled in the art and that the scope of the present disclosure is accordingly limited by nothing other than the appended claims.

The invention claimed is:

1. A digital imaging device, comprising:
a monochromatic sensor including a plurality of photosensitive elements distributed in an array, the plurality of photosensitive elements configured to convert light falling on the monochromatic sensor into electronic signals;
a lens configured to focus the light onto the monochromatic sensor;
a plurality of filter layers including a first filter layer and a second filter layer, the first filter layer having at least one filter and the second filter layer having at least one filter,
wherein the at least one filter of the first filter layer is configured to be moved into a position between the lens and the monochromatic sensor,
wherein the at least one filter of the second filter layer is configured to be moved into the position between the lens and the monochromatic sensor,
wherein the at least one filter of the first filter layer, when moved into the position between the lens and the monochromatic sensor, is configured as a single filter which covers a substantial portion of the monochromatic sensor,
wherein the at least one filter of the second filter layer, when moved into the position between the lens and the monochromatic sensor, is configured as a single filter which covers a substantial portion of the monochromatic sensor;
a storage unit; and
a processor configured to select and move the at least one filter of the first filter layer and the at least one filter of the second filter layer into the position between the lens and the monochromatic sensor,
the processor also configured to read and store the electronic signals from the plurality of photosensitive elements of the monochromatic sensor into the storage unit when the at least one filter of the first filter layer and the at least one filter of the second filter layer is moved into the position between the lens and the monochromatic sensor,
wherein the processor captures and stores a first image of the electronic signals corresponding to the at least one filter of the first filter layer from the plurality of photosensitive elements of the monochromatic sensor into the storage unit when the at least one filter of the first filter layer moved into the position between the lens and the monochromatic sensor,
wherein the processor captures and stores a second image of the electronic signals corresponding to the at least one filter of the first filter layer and the at least one filter of the second filter layer from the plurality of photosensitive elements of the monochromatic sensor into the storage unit when the at least one filter of the second filter layer is moved into the position between the lens and the monochromatic sensor,
the processor further configured to composite the stored first and second images into an output image.

2. The digital imaging device of claim 1, wherein the at least one filter of the first filter layer and the at least one filter of the second filter layer comprise a plurality of filters.

3. The digital imaging device of claim 1, wherein the first filter layer includes at least one different type of filter than the second filter layer.

4. The digital imaging device of claim 1, wherein the at least one filter of the first filter layer includes color filters.

5. The digital imaging device of claim 4, wherein the first filter layer includes at least red, green, blue, and clear color filters.

6. The digital imaging device of claim 1, wherein the at least one filter of the second filter layer includes blocking filters.

7. The digital imaging device of claim 6, wherein the blocking filters include at least ultraviolet (UV)/infra-red (IR) blocking, and clear filters.

8. The digital imaging device of claim 1, wherein the at least one filter of the second filter layer includes polarizing filters.

9. The digital imaging device of claim 1, wherein the at least one filter of the second filter layer includes neutral density filters.

10. The digital imaging device of claim 1, wherein the at least one filter of the second filter layer is configured to have the same index of refraction.

11. The digital imaging device of claim 1, wherein the at least one filter of the first filter layer is configured to have a different index of refraction than the at least one filter of the second filter layer.

12. The digital imaging device of claim 1, wherein a thickness of the first filter layer is equal to a fixed number and a thickness of the second filter is equal to the fixed number.

13. A method, comprising:
- selecting and moving a first filter of a plurality of filters of a first filter layer into a position between a lens and a monochromatic sensor;
- capturing and storing a first image of the electronic signals corresponding to the first filter from the plurality of photosensitive elements of the monochromatic sensor into a storage unit when the first filter is moved into the position between the lens and the monochromatic sensor;
- selecting and moving a second filter of a plurality of filters of a second filter layer into the position in front of the monochromatic sensor;
- capturing and storing a second image of the electronic signals corresponding to the first and second filters from the plurality of photosensitive elements of the monochromatic sensor into the storage unit when the second filter is moved into the position between the lens and the monochromatic sensor,
- wherein each of the first and second filters is a single filter covering substantial portion of the monochromatic sensor; and
- post-processing the first image and the second image by compositing the first image and the second image to produce an output image.

* * * * *